United States Patent [19] [11] 4,407,945
Gillis [45] Oct. 4, 1983

[54] CONSTITUTIVE PRODUCTION OF INTERLEUKIN 2 BY A T CELL HYBRIDOMA

[75] Inventor: Steven Gillis, Woodinville, Wash.

[73] Assignee: Immunex Corporation, Seattle, Wash.

[21] Appl. No.: 258,804

[22] Filed: Apr. 29, 1981

[51] Int. Cl.³ .................. C12P 21/00; C12P 21/02; C12N 15/00; C12N 5/00; C13R 1/91

[52] U.S. Cl. .................. 435/68; 435/70; 435/172; 435/240; 435/948

[58] Field of Search .................. 435/68, 240, 172

[56] References Cited

U.S. PATENT DOCUMENTS 4,196,265  6/1980  Koprowski et al.

OTHER PUBLICATIONS

Gillis et al., "Long Term Culture of Tumour-Specific Cytotoxic T Cells", 268 Nature 154 (1977).
Farrar et al., "Biochemical Relationship of Thymocyte Mitrogenic Factor and Factors Enhancing Humoral and Cell-Mediated Immune Responses", 121 J. Immunol. 1353 (1978).
Watson et al., "Biochemical and Biological Characterization of Lympohocyte Regulatory Molecules-I. Purification of a Class of Murine Lymphokines", 150 J. Exp. Med. 849 (1979).
Gillis et al., "Biochemical Characterization of Lymphocyte Regulatory Molecules-II. Purification of a Class of Rat and Human Lymphokines", 124 J. Immunol. 1954 (1980).
Gillis et al., "Biochemical and Biologic Characterization of Lymphocyte Regulatory Molecules-III. The Isolation and Phenotypic Characterization of Interleukin-2 Producing T Cell Lymphomas", 125 J. Immunol. 2570 (Dec. 1980).
Goldsby et al., "Hybrid Cell Lines with T-Cell Characteristics", 267 Nature 707 (1977).
Schrader et al., "A Con A-Stimulated T-Cell Hybridoma Releases Factors Affecting Haematopoietic Colony-Forming Cells and B-Cell Antibody Responses", 283 Nature 197 (1980).
Harwell et al., "A Concanavalin A Inducible, Interleukin-2 Producing T-Cell Hybridoma", 152 J. Exp. Med. 893 (1980).
Harwell et al., J. Exp. Med. 152, 893 (1980).
Gillis et al., J. Immunol. 125, 2570 (1980) in Chem., Abstr. 94:28660 (1981).

Primary Examiner—Alvin E. Tanenholtz
Assistant Examiner—James Martinell
Attorney, Agent, or Firm—Christensen, O'Connor, Johnson & Kindness

[57] ABSTRACT

A process for constitutively producing murine IL-2 from hybridoma cells generated by fusing nitrogen stimulated malignant murine cells with drug sensitive murine thymoma driver cells. A fusing agent is used to fuse the two parent cells together. After fusion, the hybrid cells are cultured in vitro in a supplemented, serum containing tissue culture medium to thereby constitutively produce IL-2. The medium also includes a group of suppressing compounds which will prevent unfused driver cells from replicating, and feeder cells used to nurture the growth of competent hybrid cells.

49 Claims, 4 Drawing Figures

HYBRID CELL LINE SUPERNATE DESIGNATION

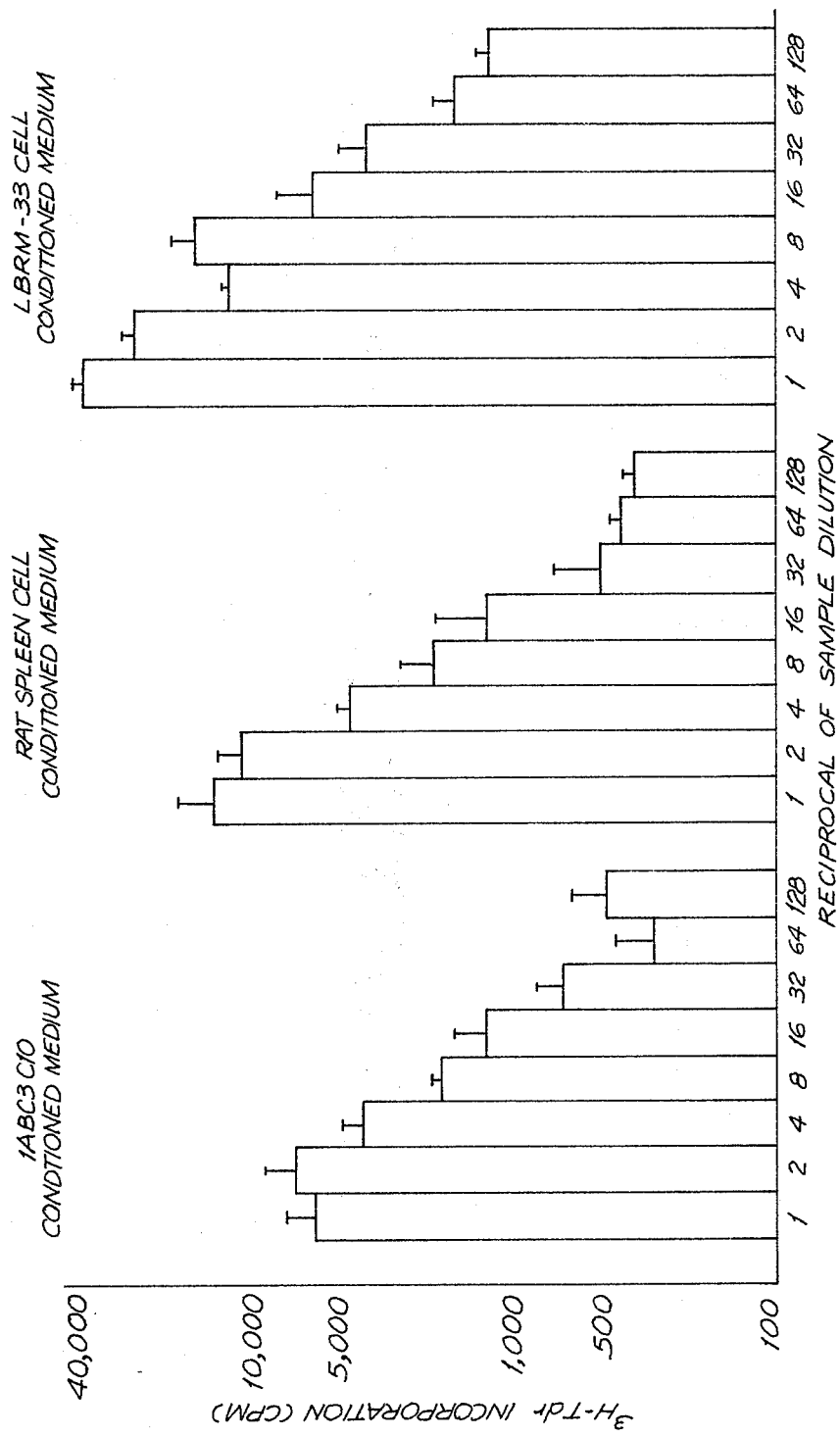

CONSTITUTIVE PRODUCTION OF INTERLEUKIN 2 BY A T CELL HYBRIDOMA

DESCRIPTION

1. Technical Field

The present invention relates to a process of preparing interleukin 2 (hereafter "IL-2") (formerly known in literature as "T Cell growth factor" or "TCGF"), and more particularly to a process for constitutively producing murine II-2 from hybrid cells formed by the fusion of murine lymphoma cells with murine IL-2 producing cells.

2. Background Art

IL-2 is a soluble protein which is capable of influencing cell-mediated immune responses in mammals, including: (1) enhancement of thymocyte mitogenesis; (2) production of alloantigen-directed cytotoxic T lymphocytes in thymocyte and nude spleen cell cultures; and (3) assistance in the generation of helper T cells in antibody responses following stimulation with hetrologous erythrocytes. In addition, IL-2 is capable both of sustaining the in vitro expotential proliferation of effector T cell lines and of inducing, both in vitro and in vivo, the generation of cytotoxic T cells from nude mouse spleens.

In the past, murine IL-2 has been produced by culturing normal rat and mouse spleen cells in tissue culture medium and stimulating the cells with a plant mitogen, such as phytohemagglutinin (hereafter "PHA") or concanavalin A (hereinafter "Con A"). However, producing murine IL-2 by mitogen stimulation of normal spleen cells results in week concentrations of Il-2. Very large volumes of IL-2 containing conditioned medium must be fractionated to produce only small quantities of purified murine IL-2. As a consequence, sufficient quantities of concentrated murine IL-2 have not been available for experimentation, nor for effective study of the molecular characterization of this immunoregulatory molecule.

Gillis et al. have recently documented a process for producing murine IL-2 from tumor cells by stimulation of the cells with a T cell mitogen. "Biochemical and Biological Characterization of Lymphocyte Regulatory Molecules-III. The Isolation and Phenotypic Characterization of Interleukin 2 Producing T Cell Lymphomas", 125 *The Journal of Immunology* 2570 (1980). A particular murine splenic lymphoma cell line from the B10. BR mouse, designated as LBRM-33, was found to produce several hundred times more IL-2 per milliliter than previously generated by mitogen stimulation of identical numbers of normal mouse splenocytes. Gillis et al., supra, also reported producing IL-2 from cloned LBRM-33 cells by culturing the cloned cells in tissue culture medium and stimulating the cells with a plant mitogen. Several of the cloned cell lines were found to produce higher concentrations of IL-2 than generated by identical numbers of the parent LBRM-33 cells.

However, in conventional procedures for producing IL-2, the T cell mitogen remains in the IL-2 containing supernate generated by mitogen stimulation of the murine cells. In the process of recovering the IL-2 from the supernate, it is important that all of the mitogen is removed. For instance, when IL-2 is used to initiate T cell line proliferation, even trace amounts of T cell mitogen can activate T cell subpopulations which will respond to IL-2 and replicate. This may result in the expression of spurious immune reactivities and specificities. Although the mitogen can be removed from the supernate, the procedure is time consuming and complicated, requiring many separate biochemical steps. Another drawback of producing IL-2 by stimulating LBRM cloned cells with a plant mitogen is that within a short time after the IL-2 containing supernate is elaborated, the productive cell line dies, thus requiring a continuous supply of productive cells to generate significant quantities of IL-2. Accordingly, a principal object of the present invention is to constitutively, i.e. without the need of a T-cell mitogen as a stimulant, produce murine IL-2 from a cell line which continues to live after elaborating IL-2 containing supernate.

Schrader et al. reported producing factors affecting haematopoietic colony-forming cells and B cell antibody responses from hybrid cells resulting from the fusion of murine T lymphoma cells, designated as "BW 5147", (obtained from a leukemic BALB/c mouse) with blast cells isolated from lymph nodes of mice immunized with keyhole limpet haemocyanin. However, the T cell mitogen, Con A, was required to be added to the culture medium to produce the factors. "A Con A-Stimulated T-Cell Hybridoma Releases Factors Affecting Haematopoietic Colony-Forming Cells and B-Cell Antibody Responses", 283 *Nature* 197 (1980). Harwell et al. in "A Concanavalin A Inducible, Interleukin 2 Producing T Cell Hybridoma", 152 *Journal of Experimental Medicine* 1893 (1980), discussed producing a hybrid cell line having T cell characteristics. The hybrid cells were formed by fusing the mouse T lymphocyte cell line, BW-5147, with Con A stimulated spleen cells. However, liberation of IL-2 activity into tissue culture supernate also required mitogen stimulation of the hybrid T cells.

DISCLOSURE OF THE INVENTION

The present invention relates to a process for constitutively producing IL-2 from a T cell hybridoma. The process includes first fusing IL-2 producing malignant murine cells with murine drug-sensitive driver cells and then culturing the resulting hybrid T cells in a medium without requiring stimulation of the hybrid T cells with a T cell mitogen. Prior to the fusion process, malignant murine IL-2 producer cells are suspended in a culture medium and stimulated with a T cell mitogen. Also prior to hybridization, murine neoplastic cells are drug-sensitized to form driver cells. The stimulated IL-2 producing malignant murine cells are mixed with the drug-sensitized driver cells and then a fusing agent added thereto to produce hybrid T cells which exhibit both the IL-2 generating capacity of the malignant murine producer cells and the immortality of the drug-sensitized driver cells.

IL-2 is constitutively produced by culturing the hybrid cells, in vitro, in a protein containing medium supplemented with various additives. A series of selective suppressor drugs are added to the medium to kill residual unfused driver cells. Prior mitogen stimulation of malignant murine IL-2 producer cells, insures that an unfused producer cell will die. Furthermore, feeder cells (thymocytes) are also added to the hybrid T cells to ostensibly provide them with nutrients. In the culturing process, IL-2 is continuously produced without the presence of a mitogen, and moreover, the hybrid cells continue to live as long as tissue culture medium is present. Another advantage of producing IL-2 in this manner is that the supernate generated in the culture does not have to be treated to remove contaminating T cell mitogen.

The process of the present invention also includes cloning murine hybrid T cell lines by suspending single cell samples of hybrid T cells found constitutively to produce IL-2 in vitro. After the single cell cultures have grown to appropriate densities, the cells are resuspended in a culture medium to generate IL-2 continuously without having to stimulate the hybrid T cells with a mitogen.

The above-described hybridizing process has been used in conjunction with a particular murine radiation-induced splenic lymphoma cell line with the B10. BR mouse, designated as LBRM-33 together with a particular murine T-lymphoma, drug-sensitized driver cell line designated as BW 5147. The IL-2 producing portion of the process of the present invention has been carried out with hybrid T cells generated by fusion of these two cell lines and by clones of such hybrid T cells. Applicant has identified a particular clonal hybrid cell line, designated as LBRM-33-1A8C3C10 (hereafter "1A8C3C10"), which is capable of constitutively producing IL-2 in concentrations approximately ten times greater than that produced by equivalent numbers of mitogen stimulated normal mouse spleen cells.

Applicant has established that an initial cell concentration of the particular hybrid T cell line used in the process of the present invention affects the level of IL-2 produced. Also, the quantity of IL-2 produced appears to be directly related to the time that the hybrid T cells are cultured in an appropriate culture medium.

Brief Description of the Drawings

The details of typical embodiments of the present invention are described in connection with the accompanying drawings in which:

FIG. 3 is a graph illustrating growth curves of CTLL cells cultured in the presence of 1A8C3C10 hybridoma cell conditioned medium and Con A-stimulated rat spleen cell conditioned medium, both adjusted to final IL-2 activity level of 2.5 units per milliliter prior to use in the CTLL growth cultures; and, FIG. 4 is a graph showing the ability of three different $\log_2$ dilution series of IL-2 conditioned media to test the ability of such conditioned media to augment mitogenesis of CBA/J6 female mice thymocytes ($2 \times 10^6$ cells per milliliter), with the three different cultures composed of: (1) 1A8C3C10 hybridoma supernate adjusted to a concentration of 10 units of IL-2 per milliliter; (2) supernate from cultures of rat spleen cells stimulated for 24 hours with Con A (5 micrograms/milliliter) and adjusted to a concentration of 30 units of IL-2 per milliliter; and (3) LDRM-33 cells stimulated by one percent (1%) by volume PHA and adjusted to a concentration of 100 units of IL-2 per milliliter.

BEST MODE OF THE INVENTION

Outline of Process

Figure 1:
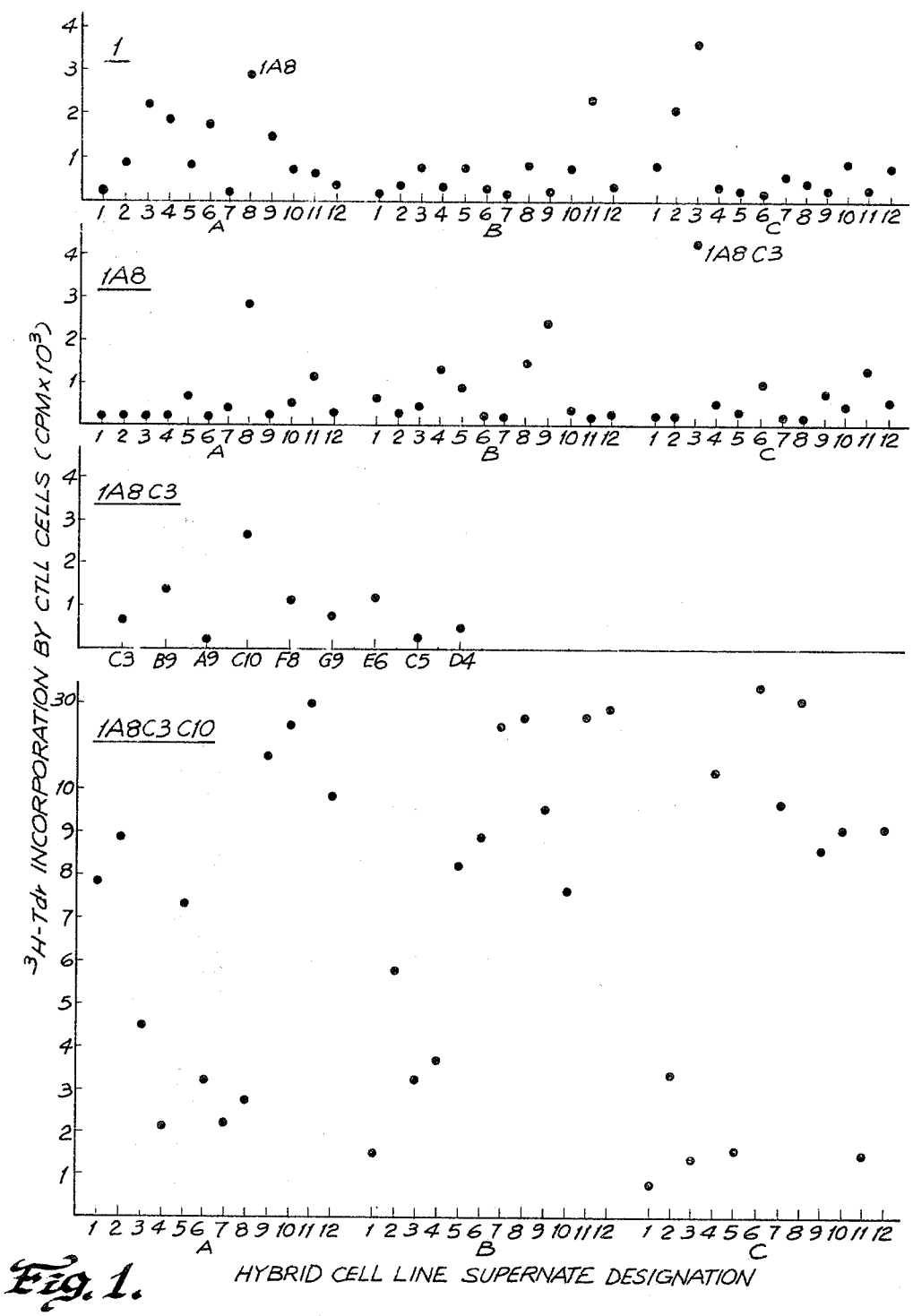
FIG. 1 is a graph illustrating the screening process used for the selection and ultimate cloning of the IL-2 producer hybridoma cell line, 1A8C3C10, with cloning trials progressing from the upper panel (identification of the 1A8 hybrid) to subcloning of the 1A8C3C10 producer hybrid cells (lowest panel)

In accordance with the present invention, murine malignant neoplastic cells are cultured in vitro in a protein containing medium and stimulated with a T cell mitogen. The mitogen stimulated cells are fused with drug-sensitive murine lymphoma driver cells by mixing the two different cells together and then adding a fusing agent. Thereafter, the mixture is pelleted, washed in a protein containing medium and the cell solution pelleted again. The resultant hybrid T cell containing pellet is next resuspended in a protein containing medium which is supplemented with various additives, feeder cells and a series of suppressor chemicals which will cause the unfused driver cells to die.

The present invention also concerns identifying potent constitutive IL-2 producing cell lines by cloning hybrid T cell lines found to produce IL-2 without requiring mitogen stimulation. Cloning is accomplished by a limiting dilution procedure wherein constitutive IL-2 producer hybrid cell lines are cultured in a supplemented, protein containing medium at a cell density of one cell per milliliter. After a period of time, the cells which produce the highest titers of IL-2 are subcloned, again by a limiting dilution method, to seek cell line sources capable of even greater IL-2 production. Once isolated, such clonal cell lines are cultured in a supplemented medium to produce IL-2 without the presence of a T cell mitogen.

The processes of the present invention have been applied to a radiation-induced splenic lymphoma cell line, designated as LBRM-33, derived from the B10.BR mouse. This murine lymphoma cell line has been fused with a hypoxanthine-aminopterin-thymidine drug (hereafter "HAT")-sensitive murine T-lymphoma cell line, designated as BW 5147, to produce several hybrid cell lines, see FIG. 1 below, capable of constitutive IL-2 production. Cloning of one of the most potent hybrid cell lines, designated as LBRM-33-1A8 (hereafter "1A8"), has resulted in the identification of various clonal hybrid T cell lines which are capable of constitutively producing IL-2 including a cell line designated as LBRM-33-1A8C3 (hereafter "1A8C3"). An even more potent IL-2 producing cell line, designated as LBRM-33-1A8C3C10 (hereafter "1A8C3C10") has been isolated by subcloning the 1A8C3 clonal cell line. A microassay of the activity level of IL-2 constitutively produced by the 1A8C3C10 cell line by use of the microassay procedure discussed by Gillis et al in "T-cell growth Factor: Parameters of Production and a Quantative Microassay for Activity", *The Journal of Immunology* 2027 (1978), has established that the elaborated supernate stimulated an IL-2 dependent T lymphocyte line (hereafter "CTLL") to incorporate in excess of 25,000 counts per minute of tritiated thymidine (hereafter "[$^3$H]Tdr]") at a final dilution of 1:10. This activity level is more than ten times the activity level of IL-2 produced by mitogen stimulation of equivalent members of normal mouse splenocytes. The results of the microassay of the supernates generated by the parent hybrid T cell line 1A8 and its clones and subclones are set forth in FIG. 1.

As outlined above, in the IL-2 production process of the present invention, prior to fusion, the IL-2 producer cells, such as the LBRM-33 lymphoma cells, are initially stimulated with a T cell mitogen. These mitogens may include various commercially available standard glycoproteins, such as PHA, Con A and pokeweed mitogen (hereafter "PKM"). Although different concentrations of a particular mitogen may be employed, applicant has found that if PHA is used, a concentration of approximately 1% by volume is adequate to stimulate the LBRM-33 lymphoma cells into IL-2 production.

The process of the present invention also involves several culturing procedures, including during: (i) initial stimulation of the parent IL-2 producer cell line with a mitogen prior to hybridization; (ii) fusion of the IL-2 producer cells and the drug-sensitive driver lymphoma cells; (iii) cloning and subcloning of the hybridoma T-cells; and (iv) constitutive IL-2 production by parent and clonal hybrid T cells, as discussed above. Various types of appropriate cell culturing media, which have been previously found to foster growth of T lymphocytes, may be utilized in these different culturing steps. These culture media include Roswell Park Memorial Institute medium 1640 (hereafter "RPMI"), Click's medium and Dulbecco Modified Eagle's medium (hereafter "DMEM").

In the production of IL-2 containing supernates from the parent and clonal hybridoma cells, the culture media may be supplemented with various individual additives, or combinations of additives, including fetal calf serum (hereafter "FCS") which has been heat-inactivated by, for example, applying heat at 56° C. for approximately 30 minutes. The quantity of FCS added may be from 2 to 10% of the total culture volume. Another additive is penicillin at a concentration range of approximately 25–250 units per milliliter, and preferably approximately 50 units per milliliter. Streptomycin also may be utilized as an additive in a preferred concentration range of from 20–250 micrograms per milliliter of total culture volume, and ideally approximately 50 micrograms per milliliter. Further additives include: (i) sodium pyruvate in a concentration range of approximately 10 to 150 millimolar and ideally approximately 100 millimolar; (ii) N-2-hydroxy-piperazine-XI$^1$-2-ethene-sulfonic acid (hereafter "HEPE'S") buffer in a preferred concentration of from 10 to 60 millimolar, and ideally approximately 25 millimolar; and (iii) fresh L-glutamine in a preferred concentration range of approximately 150–500 micrograms per milliliter, with an ideal concentration of approximately 300 micrograms per milliliter. In addition, NaHCO$_3$ at a concentration range of 1 to 30 millimolar and ideally about 16 millimolar may be added to the culture media.

The above discussed culturing processes for: (i) stimulation of an original murine malignant cell line, specifically LBRM-33 lymphoma cells; (ii) fusion of the stimulated LBRM-33 lymphoma cells with drug-marked driver lymphoma cells; and (iii) constitutive production of IL-2 from hybrid and clonal hybrid T cell lines may be carried out in various environmental conditions. Preferably, however, the cultures should be maintained at a temperature range of approximately 35° to 38° C. and in a humidified atmosphere of approximately 5 to 10% CO$_2$ in air. Also, ideally the pH of the culture medium should be kept in slightly alkaline condition, in the range of approximately pH 7.2 to 7.4.

Different types of murine driver cells may be fused with the lectin stimulated malignant murine cells to impart the hybrid T cells with the ability to proliferate after fusion. One such cell line is the mouse T lymphoma cell line, known as BW 5147, derived from the BALB/c mouse. Other driver cell lines include any T cell lymphoma selected to be 8-azoguanine/ouabain resistant. Lymphoma cells selected to be resistant to azoguanine or ouabains, are most likely sensitive to HAT, and will die when cultured in tissue culture medium containing HAT.

According to the present invention, the driver cell line is drug-marked or sensitized by conventional techniques to prevent reproduction of the driver cells. Thereafter when used in cell fusion experiments, subsequent culture of hybrid cells in tissue culture medium containing HAT, prevents unfused driver cells from proliferating. Various drugs which may be used to sensitize driver cells including the BW 5147 T lymphoma cells, include ouabain, glutathione and 8-azoguanine.

The fusion step of the present invention involves combining drug-sensitive driver cells with lectin stimulated IL-2 producing cells by placing such cells in a slightly alkaline tissue culture medium and then gradually adding a fusing agent. Fusing agents may include various types of condensation polymers of ethylene oxide and water, such as polyethylene glycol (hereafter "PEG"). Other fusing agents include DNA transforming viruses, such as Sendai viruses or the fusion protein obtained therefrom. For optimum fashion, the quantity and concentration of the fusing agent must be controlled. For instance, if PEG is used to fust lectin stimulated LBRM-33 lymphoma cells with HAT-sensitive BW 5147 cells, approximately 1 milliliter of 40% PEG (weight/volume) should be added to the tissue culture medium. However the volume of PEG may range from 0.5 to 3 milliliters and the concentrations of PEG may vary from 35% to 60% (weight/volume).

During the process of culturing the fused cells and the clones thereof, feeder cells may be added to the culture medium both to induce the proliferation of the fused cells. Although not yet definitely confirmed, it is considered that the feeder cells function to provide optimal cell density to allow small numbers of hybrid cells to multiply more readily. Also, it is thought that the feeder cells may provide the hybrid cells with nutrients required for their proliferation. Various types of feeder cells may be employed, including thymocytes from the BALB/c mouse. Other types of feeder cells include murine spleen cells, irradiated murine peritoneal exudate cells and murine macrophage cells. Feeder cells should be added to HAT containing cultures at concentrations ranging from 0.5 to $5.0 \times 10^6$ cells/milliliter with an optimal concentration of about $3 \times 10^6$ cells/milliliter.

The present invention also includes identifying potent sources of IL-2 by cloning hybrid T cell lines known constitutively to produce significant quantities of IL-2. Thereafter, the cloned hybrid T cell lines are cultured in a medium supplemented with various additives in substantially the same manner in which IL-2 is constitutively produced from hybrid 1A8 cells, as outlined above. Cloning is accomplished by a limiting dilution procedure wherein cells from parent hybrid cell lines, such as 1A8 cells, are cultured in flatbottom microplate wells. The cell are individually seeded in 100 microliter volumes of Click's medium supplemented with a 10% by volume quantity of FCS. Feeder cells, such as thymocytes from BALB/c mouse, are added to the culture medium to enhance cell growth. After approximately eight days in culture, supernates from the microplate wells which house viable cell growth are harvested and tested for IL-2 -activity.

Clonal cell lines found to produce the highest titers of IL-2, such as the hybrid cell line designated as 1A8C3, are then subcloned to seek even more potent IL-2 producing cell lines. The technique followed for subcloning is the same as used during the original cloning process, as described in the above paragraph. Use of this procedure to subclone the hybrid 1A8C3 cells has led to the identification of an even more potent IL-2 producing cell line, designated as 1A8C3C10. As illustrated in FIG. 1, the 1A8C3C10 cell line was found to produce even greater quantities of IL-2 than generated by the same number of 1A8C3 cells as indicated by a higher level of [$^3$H]Tdr incorporation.

Figure 2:
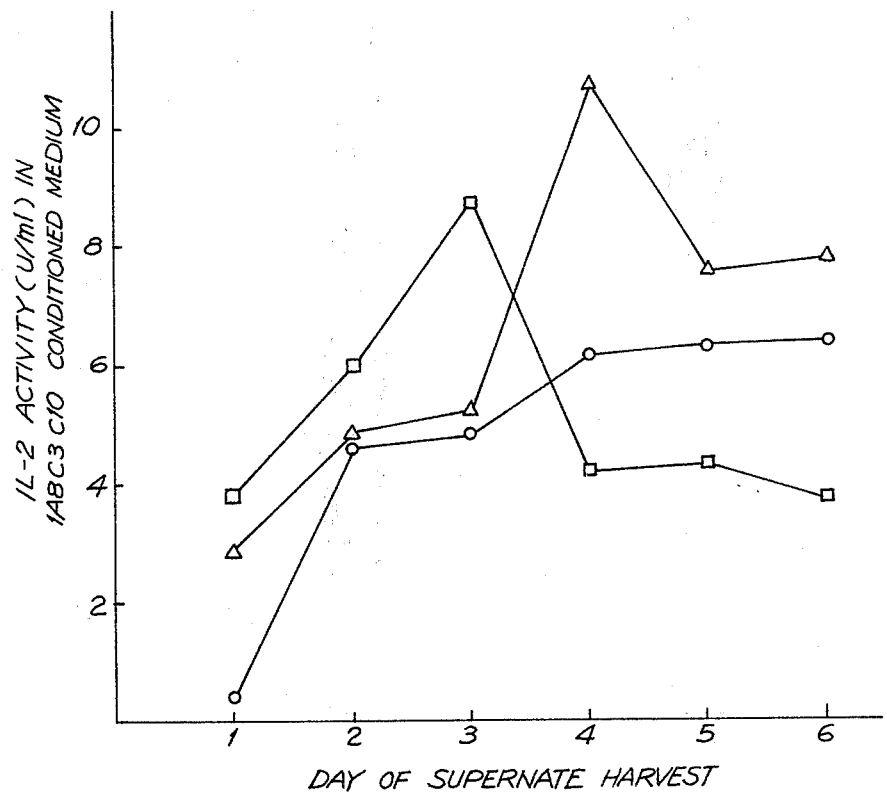
FIG. 2 is a graph illustrating units of IL-2 activity per milliliter for various initial cell concentrations of the 1A8C3C10 cell line that were cultured for various numbers of days in Click's medium supplemented with ten percent (10%) by volume FSC.
Figure 9:
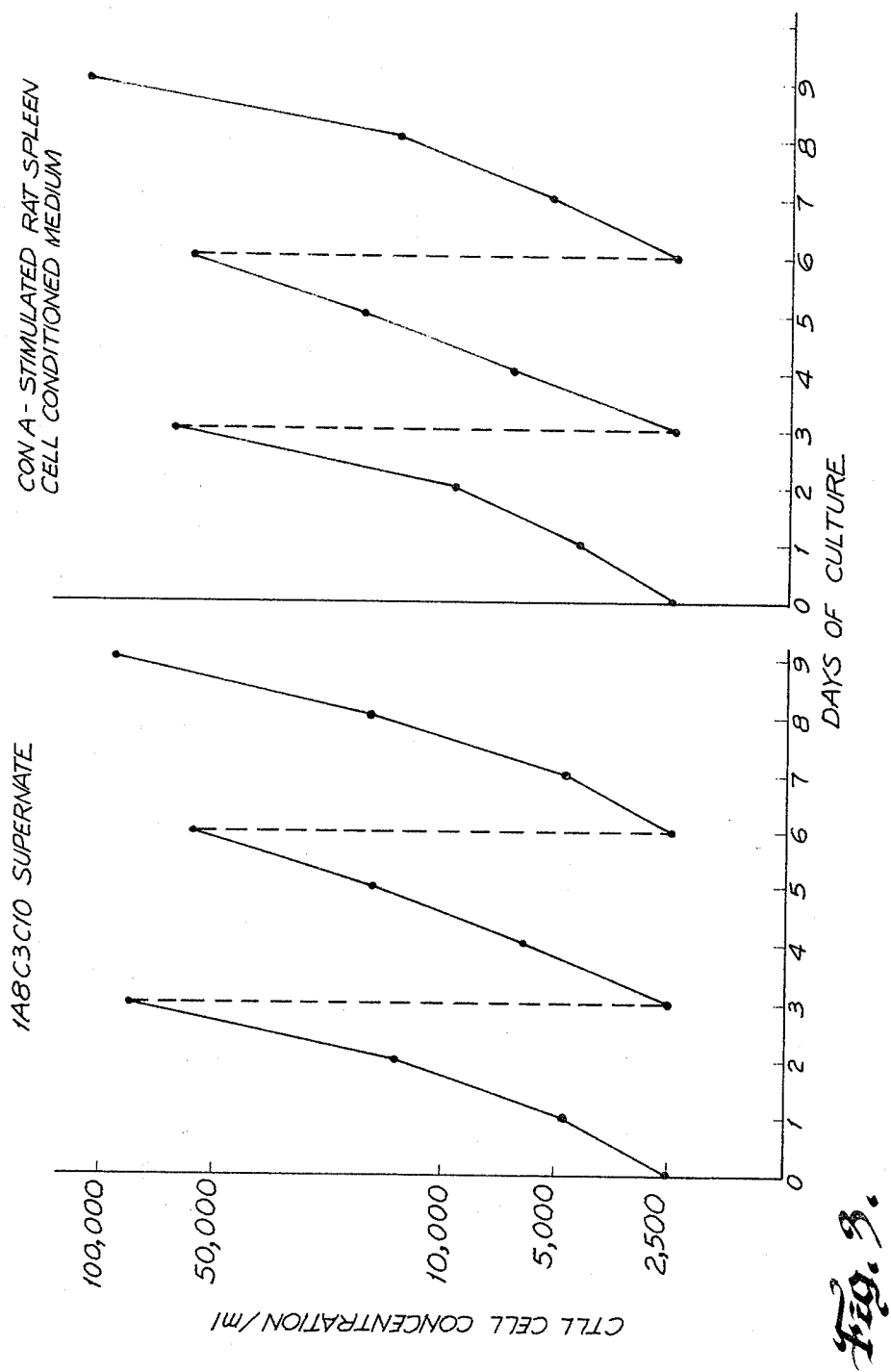

Applicant has found that the initial cell density of a particular hybridoma cell line used in the culture process affects the quantity of IL-2 constitutively produced per number of initial cells. For instance, as set forth in FIG. 2, using the 1A8C3C10 hybrid cell line, when a concentration of $1 \times 10^5$ 1A8C3C10 cells per milliliter are cultured with Click's medium supplemented with 10% by volume FCS in 10 milliliter volumes (25 square centimeter tissue culture flasks, #3013, Falcon Plastics. Oxnard, CA), approximately 6 units of IL-2 activity per milliliter are produced after four days of culture. When the initial cell concentration is increased to approximately $5 \times 10^5$ cells per milliliter, a maximum of approximately 10 units of IL-2 per milliliter are produced. If, however, the concentration of 1A8C3C10 cells is further increased to, for instance $1 \times 10^6$ cells per milliliter, the production of IL-2 drops back down to approximately 4 units per milliliter. Thus, if 1A8C3C10 cells are used to produce IL-2, the initial cell density preferably should be in the range of about $3 \times 10^5$ cells per milliliter to $7 \times 10^5$ cells per milliliter with an ideal concentration of approximately $5 \times 10^5$ cells per milliliter.

The quantity of IL-2 constitutively generated by the hybrid murine cells produced by the present invention varies with time. For instance, when $5 \times 10^5$ 1A8C3C10 cells per milliliter are cultured in Click's medium supplemented with 10% by volume FCS, approximately 3 units per milliliter of IL-2 activity are generated after twenty-four hours of culturing, see FIG. 2. At three days, IL-2 activity increases to approximately 5 units per milliliter. A peak level of approximately 10 units per milliliter of IL-2 activity is obtained after four days of culturing. Thus, the optimal culture duration for constitutively producing IL-2 from 1A8C3C10 clonal hybrid T cells is approximately from three to five days.

Microassay of IL-2

The level of IL-2 produced by the hybridoma culture supernates of the present and clonal hybrid cells of the present invention (to ascertain, for example, what cell lines produce significant levels of IL-2), may be tested by using the microassay procedure discussed by Gillis et al in "T-Cell Growth Factor: Parameters or Production and a Quantatative Microassay for Activity", 120 *The Journal of Immunology*, 2027 (1978). The assay monitors the IL-2 dependent cellular proliferation of a mouse cytotoxic T cell line (hereafter "CTLL"). Once potent hybrid cell lines are identified, such as 1A8C3C10 cells, the microassay technique is then employed to determine optimum culture conditions for IL-2 production, such as optimum initial cell concentrations of 1A8C3C10 and optimum harvest times, as discussed above.

Briefly, the microassay procedure includes seeding approximately $4 \times 10^4$ CTLL cells in a $\log_2$ dilution series of potential IL-2-containing hybrid supernate samples. In each culture, approximately $4 \times 10^4$ CTLL cells are suspended in Click's medium supplemented with 10% by volume FCS to thereby form 200 microliter volumes. The cultures are incubated for approximately 20 hours at 37° C. in a humidified atmosphere of 5% carbon dioxide in air. Thereafter, the cultures are pulsed for approximately four hours with 0.5 microcurie of [$^3$H]Tdr having a specific activity of 20 millicures per millimole (obtained from New England Nuclear, Boston, MA). After pulsing, the cultures are harvested onto glass fiber filter strips, for instance with the aid of a multiple automated sample harvester. [$^3$H]Tdr incorporation by the CTLL cells is measured by liquid scintillation counting. By this procedure, the CTLL cells which are exposed to IL-2 will incorporate [$^3$H]Tdr in a dose-dependent manner. CTLL cells cultured in the absence of IL-2 will incorporate only scintillant control levels of $^3$[H]Tdr and will be more than 95% trypan-blue positive after 24 hours of IL-2 deprivation, indicating that such cells are dead. Units of IL-2 activity are determined by Probit analysis of [$^3$H]Tdr incorporation data, as described above. A 1 unit per milliliter standard of IL-2 activity is defined as the amount of IL-2 activity present in a forty-eight hour tissue culture medium conditioned by Con A (2.5 micrograms/milliliter) stimulation of an initial concentration of $10^6$ cells per milliliter of normal rat spleen cells, A 1 unit per milliliter standard of IL-2 activity routinely stimulates approximately 2500 counts per minute of CTLL [$^3$H]Tdr incorporation at a dilution of 1:20. The results of the microassays of the supernates produced by the various hybrid T cell lines are set forth in FIG. 1.

Confirmation of the Presence of IL-2 in Hybridoma Culture Supernates

In addition to the above-described microassay procedure, the presence of IL-2 in the hybridoma culture supernates was further substantiated by testing their capacity to support long-term growth of CTLL cells. This test is of significance, since one of the potential uses of a constitutive IL-2 producer hybridoma is to generate conditioned medium which is capable of supporting the in vitro growth of cloned effector T cell lines. In the test procedure, hybrid supernates containing 5 units per milliliter of IL-2 activity were dialysed into complete RPMI 1640 medium to replenish nutrients lost during IL-2 production by hybrid cell metabolism. Next, CTLL cultures were prepared by seeding two milliliter cultures of CTLL cells in concentrations of $2.5 \times 10^3$ cells per milliliter in flat-bottomed cluster plate wells (#3024, Costar, Inc., Cambridge, MA). Each of the cultures contained either 50% by volume 1A8C3C10 dialyzed conditioned medium or a 50% by volume rat spleen cell conditioned medium to serve as a conrol sample. The rat spleen cell conditioned medium was produced by a concentration of $10^7$ rat spleen cells per milliliter stimulated for 24 hours by a concentration of 5 micrograms per milliliter of Con A. Both the hybridoma and the rat spleen cell conditioned medium were adjusted to final IL-2 activity level of 2.5 units per milliliter prior to use in the CTLL growth cultures. Cell samples from both cultures were harvested daily to ascertain their growth rate and their viability was measured by trypan blue dye exclusion. When the CTLL cells reached a density of approximately $1 \times 10^5$ cells per milliliter, concentrations of $2.5 \times 10^3$ of the CTLL cells per milliliter were subcultured in fresh 2 milliliter tissue culture medium, each containing 25 units per milliliter of IL-2 derived from the appropriate source of IL-2 activity, e.g. 1A8C3C10 hybrid cell dialyzed conditioned medium or rat spleen cell conditioned medium.

As illustrated in FIG. 3, both the CTLL cells grown in standard IL-2 containing medium or in 1A8C3C10 supernates exhibited identical growth patterns over a nine day culture. The CTLL cell samples cultured in both IL-2 sources doubled on both the first and second days of culture and increased to nearly 10-fold of their original cell density by the third day. The correspondence between the proliferation of the CTLL cells in the two different conditioned media verifies the existence of IL-2 activity in 1A8C3C10 supernates. Furthermore, no difference in cell viability was observed between CTLL cells cultured in rat spleen cell conditioned medium or in 1A8C3C10 hybridoma cell conditioned medium, in both instances more than 90% viability was observed on ach day of culture.

To further confirm the presence of IL-2 activity, the supernates of the hybrid T cells and of the clones thereof were tested for their capacity to enhance thymocyte mitogenesis, another biologic activity which is attributed to IL-2. The test included seeding concentrations of approximately $2\times10^5$ cells per milliliter of thymocyte cells prepared from CBA/J6 female mice, (8-10 weeks of age, Jackson Laboratories, Bar Harbor, Maine) in three different $\log_2$ dilution series of IL-2 conditioned media to test the ability of such conditioned media to augment mitogenesis of the CBA/J6 thymocytes. The three different cultures included: (1) 1A8C3C10 hybridoma supernate adjusted to a concentration of 10 units of IL-2 per milliliter; (2) supernate from cultures of rat spleen cells stimulated for 24 hours with Con A (5 micrograms/milliliter) and adjusted to a concentration of 30 units of IL-2 per milliliter; and (3) LBRM-33 cells stimulated by 1% by volume PHA and adjusted to a concentration of 100 units of IL-2 per milliliter. Each of the thymocyte cultures were 200 microliters in total volume and were composed of Click's medium, 10% by volume FCS and a concentration of 2 micrograms per milliliter of Con A. After 72 hours of culture, each of the cultures was exposed to 0.5 microcuries of [$^3$H]Tdr as detailed above in the discussion relating to "Microassay of IL-2". Thereafter, the thymocytes were harvested and cell proliferation measured by liquid scintillation counting. As indicated in FIG. 4, the 1A8C3C10 supernate, the LBRM-33 conditioned medium and the conventionally prepared rat conditioned medium all significantly enhanced Con A induced thymocyte proliferation, thereby confirming that 1A8C3C10 supernate in fact contained IL-2. Moreover, the test results indicated that enhancement of the Con A stimulated thymocyte mitogenesis is related to the IL-2 activity of the given condition medium since [$^3$H]Tdr incorporation proportionally decreased with increased dilution of all three different types of condition media.

Confirmation of 1A8C3C10 Hybrid Origin

Through phenotypic characterization, the 1A8C3C10 hybrid clonal cells were found to express both Thy 1.1 and Thy 1.2 differentiation antigens. The LBRM-33 cells are known to display the Thy 1.2 antigen but not the Thy 1.1 antigen. Conversely, the BW 5147 cells are known to express the Thy 1.1 antigen but not the Thy 1.2 antigen. Thus, the expression of both cell surface markers by the 1A8C3C10 hybrid T cell line confirms that this hybridoma cell was a product of the fusion of LBRM-33 cells with BW 5147 tumor cells.

EXAMPLE 1

LBRM-33 murine leukemic tumor cells were stimulated for 12 hours with a 1.0% by volume concentration of PHA (PHA, Grand Island Biochemical Company, Grand Island, NY) in a tissue culture medium composed of 20 milliliters of RPMI 1640 medium supplemented with 5% by volume, heat-inactivated (56√ C. for thirty minutes) FCS. The culture was maintained at approximately 37° C. in a humidified atmosphere of 5% carbon dioxide in air. After PHA stimulation, the LBRM-33 lymphoma cells were washed several times with a mixture composed of RPMI 1640 and 5% by volume heat-inactivated FCS.

After the washing procedure, the LBRM-33 cells were fused with the BW 5147 cells by mixing approximately $2\times10^7$ of the PHA-stimulated LBRM-33 cells with approximately $5\times10^6$ drug-marked BW 5147 driver cells. The cellular mixture was pelleted by centrifuging for five minutes at $160\times$ g. One milliliter mixture of 40% (weight/volume) PEG in RPMI 1640 (pH 7.2) was gradually added to the fusin pellet. The PEG treated cell mixture was then pelleted again by centrifuging for twelve minutes at $300\times$ g. Next, the pellet was resuspended by carefully adding, over a 5–7 minute period, 10 milliliters of RPMI 1640 supplemented with 10% by volume FCS. This cell solution was then pelleted a final time by centrifuging for five minutes at $160\times$ g.

Constitutive IL2 production by the hybridoma cells derived from the fusion of parent LBRM-33 cells and BW 5147 cells was achieved by culturing the cell pellet resulting from the last centrifugation procedure, set forth in the above paragraph. The cell pellet was suspended in 100 milliliters of Click's medium supplemented with 10% by volume, heat-inactivated (56° C. for 30 minutes) FCS, 100 millimolar of sodium pyruvate, 25 millimolar of Hepe's buffer, 16 millimolar of NaHCO$_3$, 50 units per milliliter of penicillin, 50 micrograms per milliliter of streptomycin and 300 micrograms per milliliter of fresh L-glutamine. Approximately $2\times10^8$ BALB/c thymocyte cells were added to the cell suspension to serve as filler cells. To prevent growth of unfused BW 5147 driver cells, suppressing agents (HAT) composed of 13.6 micrograms of hypoxanthine per milliliter of medium, 0.176 micrograms of aminopterin per milliliter of culture and 3.88 micrograms of thymidine per milliliter of culture. The entire cell population and medium was then divided into individual 200 microliter aliquots in flat-bottomed microplate wells (No. 3596, Costar, Inc., Data Packaging, Cambridge, MA). The cultures were all maintained at approximately 37° C. in a humidified atmosphere of 5% CO$_2$ in air. Periodically, the supernates from the microculture wells that were found to contain hybrid cell growth were assayed for IL-2 activity using the microassay procedure as discussed above.

EXAMPLE 2

IL-2 was constitutively produced by culturing a concentration of $5\times10^5$ 1A8C3C10 cells per milliliter in 25 cm$^2$ tissue culture flasks (#3013, Falcon Plastics, Oxnard, CA) in 5 milliliter aliquots of HAT-containing Click's medium. The medium was supplemented with 10% by volume, heat-inactivated (56° C. for 30 minutes) FCS, 100 millimolar of sodium pyruvate, 25 millimolar of Hepe's buffer, 16 millimolar of NaHCO$_3$, 50 units per milliliter of penicillin, 50 microgram per milliliter streptomycin and 300 micrograms per milliliter of fresh L-glutamine. The culture was maintained at approximately 37° C. in a humidified atmosphere of 5% CO$_2$ in air. Four days later, the supernate was found to contain 19–20 units/milliliter of IL-2 activity.

As will be apparent to those skilled in the art to which the invention is addressed, the present invention may be carried out by using hybrid T cell lines, culture media, culture media additives, mitogen stimulants, drug-sensitizers, fusing agents and suppressing agents other than those specifically disclosed above, without departing from the spirit or essential characteristics of the invention. The particular processes described above are therefore to be considered in all respects as illustrative and not restrictive, i.e. the scope of the present invention is as set forth in the appended claims rather than being limited to the examples of the IL-2 producing processes as set forth in the foregoing description.

What is claimed is:

1. A process for constitutively producing murine interleukin-2, comprising:
stimulating murine mononuclear leukocytes in a first culture medium containing a T cell mitogen stimulant;
marking murine neoplastic cells with a sensitizing drug to produce driver cells;
fusing said murine mononuclear leukocyte cells with said driver cells to produce a hybridoma capable of constitutively producing interleukin-2; and
culturing the hybridoma cells in a second culture medium, containing selective suppressing agents which allow only hybrid cells to proliferate.

2. The process of claim 1, wherein the murine mononuclear leukocytes include malignant murine cells.

3. The process of claim 2, wherein said malignant cells are T leukemic cells or T lymphoma cells.

4. The process of claim 3, wherein said T lymphoma cells are LBRM-33 cells.

5. The process of claim 4, wherein said T lymphoma cells are clones of said LBRM-33 cells.

6. The process of claim 3, wherein said malignant cells are clones of said T lymphoma cells.

7. The process of claim 6, wherein said clones of T lymphoma cells are clones of LBRM-33 lymphoma murine T cells.

8. The process of claim 1, wherein said T cell mitogen in said first culture medium is a compound selected from the group consisting of phytohemagglutinin, concanavalin A, and pokeweed mitogen.

9. The process of claim 8, wherein said first culture medium includes Roswell Park Memorial Institute medium 1640.

10. The process of claim 8, wherein said first culture medium includes Click's medium or Dulbecco Modified Eagle's medium.

11. The process of claim 1, wherein said first culture medium is a compound selected from the group consisting of Roswell Park Memorial Institute medium 1640, Click's medium and Dulbecco Modified Eagle's medium.

12. The process of claim 2, wherein said T cell mitogen in said first culture medium is a compound selected from the group consisting of phytohemagglutinin, concanavalin A and pokeweed mitogen.

13. The process of claim 12, wherein said first culture medium includes Roswell Park Memorial Institute medium 1640.

14. The process of claim 12, wherein said first culture medium includes Click's medium or Dulbecco Modified Eagle's medium.

15. The process of claim 3, wherein said T cell mitogen in said first culture medium is a compound selected from the group consisting of phytohemagglutinin, concanavalin A and pokeweed mitogen.

16. The process of claim 15, wherein said first culture medium includes Roswell Park Memorial Institute medium 1640.

17. The process of claim 15, wherein said first culture medium includes Click's medium or Dulbecco Modified Eagle's medium.

18. The process of claim 1, wherein said murine driver cells include drug marked, ouabain or 8-azaguanine resistant, malignant T cells.

19. The process of claim 18, wherein said driver cells include drug marked BW 5147 thymocytes.

20. The process of claim 18, wherein said sensitizing drug is a compound selected from the group consisting of ouabain, glutathione and 8-azaguanine.

21. The process of claim 1, wherein the step of fusing the murine mononuclear leukocyte cells with drug sensitive driver cells includes mixing the murine mononuclear leukocyte cells with the drug sensitive driver cells, and adding a fusion compound selected from the group consisting of polyethylene glycol and deoxyribonucleic acid transforming viruses.

22. The process of claim 21, wherein said deoxyribonucleic acid transforming viruses include Sendai virus or the fusion protein obtained therefrom.

23. The process of claim 21, wherein said fusion compound further includes a third tissue culture medium.

24. The process of claim 23, wherein said third tissue culture medium includes Roswell Park Memorial Institute medium 1640, Click's medium or Dulbecco Modified Eagle's medium.

25. The process of claim 1, wherein said second culture medium includes a compound selected from a group consisting of Roswell Park Memorial Institute medium 1640, Click's medium or Dulbecco Modified Eagle's medium.

26. The process of claim 25, wherein said second culture medium contains one or more compounds selected from the group consisting of fetal calf serum, sodium pyruvate, Hepe's buffer, NaHCO$_3$, penicillin, streptomycin and L-glutamine.

27. The process of claim 26, wherein said second culture medium includes suppressing agents to preclude the growth of unfused driver cells.

28. The process of claim 27, wherein said suppressing agents include one or more compounds selected from the group consisting of hypoxanthine, aminopterin and thymidine.

29. The process of claim 25, wherein said second culture medium further includes feeder cells.

30. The process of claim 29, wherein said feeder cells includes cells selected from the group consisting of murine thymocytes, murine spleen cells, irradiated murine peritoneal exudate cells and murine macrophages.

31. The process of claim 25, wherein said second culture medium further includes feeder cells.

32. The process of claim 1, further including the step of cloning said hybridoma cells.

33. The process of claim 32, wherein said hybridoma cells are cloned in a fourth culture medium.

34. The process of claim 33, wherein said fourth culture medium includes a compound selected from the group consisting of Roswell Park Memorial Institute medium 1640, Click's medium and Dulbecco Modified Eagle's medium.

35. The process of claim 34, wherein said fourth culture medium contains one or more compounds selected from the group consisting of fetal calf serum, sodium pyruvate, Hepe's buffer, $NaHCO_3$, penicillin, streptomycin and L-glutamine.

36. The process of claim 34, wherein said fourth culture medium further includes feeder cells.

37. The process of claim 36, wherein said feeder cells include cells selected from the group consisting of murine thymocytes, murine spleen cells, irradiated murine peritoneal exudate cells and murine microphages.

38. A process for producing IL-2 from a hybrid murine T cell line, comprising culturing in a tissue culture medium, hybrid T cells capable of constitutively producing IL-2, said hybrid cells produced by fusing mitogen stimulated, malignant murine IL-2 producer cells with drug marked murine driver cells.

39. The process of claim 38, whereinsaid malignant murine IL-2 producer cells are T leukemic or T lymphoma cells.

40. The process of claim 39, wherein said T lymphoma cells are LBRM-33 cells.

41. The process of claim 40, wherein said T lymphoma cells are clones of said LBRM-33 cells produced by separating said LBRM-33 cell line into individual cells and then culturing the individual cells in a culture medium.

42. The process of claim 38, wherein said murine driver cells are T leukemic cells or T lymphoma cells.

43. The process of claim 42, wherein said murine lymphoma cells are BW 5147 cells.

44. The process of claim 38, wherein said hybrid T cells are clones derived from parent hybrid T cells produced by fusion of murine, mitogen stimulated, IL-2 producer cells with drug-sensitive murine driver cells.

45. The process of claim 38, wherein said culture medium includes a compound selected from the group consisting of Roswell Park Memorial Institute medium 1640, Click's medium, and Dulbecco Modified Eagle's medium.

46. The process of claim 45, wherein said culture medium further includes driver cell suppressing agents to prevent proliferation of uncoupled driver cells.

47. The process of claim 46, wherein said suppressing agents include hypoxanthine, aminopterin and thymidine.

48. The process of claim 45, wherein said culture medium further includes feeder cells.

49. The process of claim 48, wherein said feeder cells include cells selected from the group consisting of murine thymocytes, murine spleen cells, irradiated murine peritoneal exudate cells and murine macrophages.

* * * * *

UNITED STATES PATENT AND TRADEMARK OFFICE
CERTIFICATE OF CORRECTION

PATENT NO. : 4,407,945
DATED : October 4, 1983
INVENTOR(S) : Steven Gillis

It is certified that error appears in the above-identified patent and that said Letters Patent is hereby corrected as shown below:

On the title page;

Abstract   line 2: "nitrogen" should be --mitogen--.
Column 1,  line 33: "week" should be --weak--.
Column 4,  lines 52-3: "Quantative" should be --Quantitative--
Column 6,  line 24: "fashion" should be --fusion--.
Column 6,  line 61: "cell" should be --cells--.
Column 7,  line 52: "present" should be --parent--.
Column 7,  line 57: "Quantatative" should be --Quantitative--.
Column 8,  line 21: "Probit" should be --probit--.
Column 8,  line 55: "conrol" should be --control--.
Column 8,  line 68: "25" should be --2.5--.
Column 10, line 10: "56  " should be --56°--.

Signed and Sealed this

Twenty-second Day of October 1985

[SEAL]

Attest:

DONALD J. QUIGG

Attesting Officer

Commissioner of Patents and
Trademarks—Designate